United States Patent
Toyama

(10) Patent No.: US 10,289,983 B2
(45) Date of Patent: May 14, 2019

(54) APPARATUS FOR MANAGING REPAIR INFORMATION OF MEDICAL EQUIPMENT, METHOD FOR OPERATING THE SAME, AND REPAIR INFORMATION MANAGEMENT SYSTEM

(71) Applicant: FUJIFILM Corporation, Tokyo (JP)

(72) Inventor: Kazunari Toyama, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 653 days.

(21) Appl. No.: 14/526,275

(22) Filed: Oct. 28, 2014

(65) Prior Publication Data

US 2015/0120318 A1 Apr. 30, 2015

(30) Foreign Application Priority Data

Oct. 30, 2013 (JP) ................. 2013-225416

(51) Int. Cl.
*G06Q 50/00* (2012.01)
*G06Q 10/00* (2012.01)
(Continued)

(52) U.S. Cl.
CPC ............. *G06Q 10/20* (2013.01); *G06F 19/00* (2013.01); *G16H 40/40* (2018.01)

(58) Field of Classification Search
CPC ........ G06Q 50/22; G06Q 50/24; G06Q 40/08; G06Q 10/10; G06F 19/322; G06F 17/30;
(Continued)

(56) References Cited

U.S. PATENT DOCUMENTS

| 2009/0284348 A1* | 11/2009 | Pfeffer | G08B 25/006 340/7.3 |
| 2010/0312605 A1* | 12/2010 | Mitchell | G06Q 10/06 705/7.13 |
| 2014/0074730 A1* | 3/2014 | Arensmeier | F24F 11/0086 705/305 |

FOREIGN PATENT DOCUMENTS

| CN | 101233544 A | 7/2008 |
| CN | 103279831 A | 9/2013 |

(Continued)

OTHER PUBLICATIONS

Japanese Office Action dated Dec. 9, 2015 with an English translation thereof.

(Continued)

*Primary Examiner* — Tran N Nguyen
(74) *Attorney, Agent, or Firm* — McGinn I.P. Law Group, PLLC.

(57) ABSTRACT

A repair information management apparatus, which manages repair information of endoscopes, receives repair information of an endoscope from a user terminal in a repair center where a repair technician repairs the endoscope, and stores the repair information for each repair. When the user terminal requests for a skill evaluation screen of a specific repair technician, the repair information management apparatus reads out the repair information of the repairs performed by the repair technician and generates the skill evaluation screen and delivers it to the user terminal. The skill evaluation screen includes a skill evaluation table that shows, for the repair technician, a record of the repairs for each model of the endoscope and a record of the repairs for each difficulty level of a description of the repair.

8 Claims, 19 Drawing Sheets

38

CODE CORRESPONDENCE TABLE

| POSITIONS, DESCRIPTIONS, AND CAUSES OF FAILURE | REPAIR DESCRIPTIONS |
|---|---|
| P001(CLEANING NOZZLE), F001(MALFUNCTION), C001(IMPACT) | R001(ADJUST CLEANING NOZZLE) |
| P001(CLEANING NOZZLE), F001(MALFUNCTION), C002(DAMAGE BY WATER) | |
| P001(CLEANING NOZZLE), F003(WATER LEAKAGE), C001(IMPACT) | R002(REPLACE CLEANING NOZZLE) |
| P001(CLEANING NOZZLE), F003(WATER LEAKAGE), C002(DAMAGE BY WATER) | |
| P002(ANGLE KNOB), F001(MALFUNCTION), C001(IMPACT) | R003(REPLACE ANGLE KNOB) |
| ⋮ | ⋮ |

(51) Int. Cl.
*G16H 40/40* (2018.01)
*G06F 19/00* (2018.01)

(58) Field of Classification Search
CPC ........ G06F 19/30; G06F 19/32; G06F 19/321;
G06F 19/324; G06F 19/325; G06F
19/326; G06F 19/328; G06F 19/34; G06F
19/3418; G06F 19/3456; G06F 19/3462;
G06F 19/3468; G06F 19/3475; G06F
19/3481; G06F 19/36; A61N 1/08; G16H
10/10; G16H 10/20; G16H 10/40; G16H
10/60; G16H 10/65; G16H 15/00; G16H
20/00; G16H 20/10; G16H 20/13; G16H
20/17; G16H 20/30; G16H 20/40; G16H
20/60; G16H 20/70; G16H 20/90; G16H
30/00; G16H 30/20; G16H 30/40; G16H
40/00; G16H 40/20; G16H 40/40; G16H
40/60; G16H 40/63; G16H 40/67; G16H
50/00; G16H 50/20; G16H 50/30; G16H
50/50; G16H 50/70; G16H 50/80; G16H
70/00; G16H 70/20; G16H 70/14; G16H
70/60; G16H 80/00
See application file for complete search history.

(56) References Cited

FOREIGN PATENT DOCUMENTS

| | | |
|---|---|---|
| JP | 2002-15082 A | 1/2002 |
| JP | 2006-092200 A | 4/2006 |
| JP | 2006-106861 A | 4/2006 |
| JP | 2011-129055 A | 6/2011 |
| WO | WO 02/03276 A1 | 1/2002 |

OTHER PUBLICATIONS

Chinese Office Action dated Oct. 31, 2018, in corresponding Chinese Patent Application No. 201410598929.9, with an English translation therof.

* cited by examiner

FIG. 2

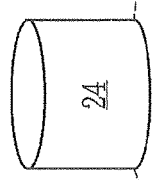
24

REPAIR INFORMATION

| No. | ID | SERIAL No. | CLIENT | NAME | TECHNICIAN ID | RE-REPAIR | IN | OUT | P-Code | F-Code | C-Code | R-Code |
|---|---|---|---|---|---|---|---|---|---|---|---|---|
| 1 | 1234 | 32422 | HOSPITAL A | SUZUKI | E01234 | PRESENT | 13/08/01 | 13/09/20 | P001 | F001 | C001 | R001 |
| 2 | 13D-3 | 30A425 | HOSPITAL C | SATO | E02612 | NIL | 13/10/12 | 13/12/14 | P001 | F001 | C002 | R002 |
| ... | ... | ... | ... | ... | ... | ... | ... | ... | ... | ... | ... | ... |

REPAIR DESCRIPTIONS

| R-Code | DESCRIPTIONS |
|---|---|
| R001 | ADJUST NOZZLE |
| R002 | REPLACE NOZZLE |
| R003 | REPLACE ANGLE KNOB |
| ... | ... |

CAUSES OF FAILURE

| C-Code | DESCRIPTIONS |
|---|---|
| C001 | IMPACT |
| C002 | DAMAGE BY WATER |
| C003 | POOR CONTACT |
| ... | ... |

FAILURE DESCRIPTIONS

| F-Code | DESCRIPTIONS |
|---|---|
| F001 | MALFUNCTION |
| F002 | NOISE |
| F003 | WATER LEAKAGE |
| ... | ... |

FAULTY PARTS

| P-Code | DESCRIPTIONS |
|---|---|
| P001 | CLEANING NOZZLE |
| P002 | ANGLE KNOB |
| ... | ... |

FIG. 4

CODE CORRESPONDENCE TABLE

| POSITIONS, DESCRIPTIONS, AND CAUSES OF FAILURE | REPAIR DESCRIPTIONS |
|---|---|
| P001 (CLEANING NOZZLE), F001 (MALFUNCTION), C001 (IMPACT) | R001 (ADJUST CLEANING NOZZLE) |
| P001 (CLEANING NOZZLE), F001 (MALFUNCTION), C002 (DAMAGE BY WATER) | R002 (REPLACE CLEANING NOZZLE) |
| P001 (CLEANING NOZZLE), F003 (WATER LEAKAGE), C001 (IMPACT) | |
| P001 (CLEANING NOZZLE), F003 (WATER LEAKAGE), C002 (DAMAGE BY WATER) | |
| P002 (ANGLE KNOB), F001 (MALFUNCTION), C001 (IMPACT) | R003 (REPLACE ANGLE KNOB) |
| ... | ... |

FIG. 5

TERM CORRESPONDENCE TABLE

| ITEM | English | Japanese | Portuguese | |
|---|---|---|---|---|
| APPLIED CAP NAME | Applied CAP Name | 適用CAP名称 | | ... |
| ATTACH INSPECTION SHEET | Inspection Sheet | | | ... |
| DEFECTS | Defects | 不具合 | Difeito | ... |
| DEFECT CAUSES | Causes | 不具合原因 | Causa | ... |
| DEF CASE CODE | F-Code | F-Code | F-Code | ... |
| DEF CAUSE CODE | C-Code | C-Code | C-Code | ... |
| DEF POS CODE | P-Code | P-Code | P-Code | ... |
| DISP PRT PICT5 | Video Image | ビデオ画像 | Foto da Imagem | ... |
| DISP PRT PICT6 | Video Image | ビデオ画像 | Foto da Imagem | ... |
| REPAIR ACTIONS | Repairs | 修理作業 | Reparos | ... |
| ... | ... | ... | ... | ... |

39 USER CORRESPONDENCE TABLE

| USER NAME | USER ID | LANGUAGE | LANGUAGE ID |
|---|---|---|---|
| USER A | 123469 | JAPANESE | JPN |
| USER B | 100235 | ENGLISH | ENG |
| USER C | 369852 | PORTUGUESE | POR |
| ⋮ | ⋮ | ⋮ | ⋮ |

FIG. 7

MODEL ID CORRESPONDENCE TABLE 40

| MODEL | MODEL ID |
|---|---|
| Ultr (ULTRASONIC ENDOSCOPE) | ○○○-○○ |
| | ×××-×× |
| Zoom (MAGNIFYING ENDOSCOPE) | △△△-△△ |
| | □□□-□□ |
| Bro (BRONCHOSCOPE) | ○△○-△△ |
| | ×□×-□□ |
| Duo (DUODENOSCOPE) | □△○-△□ |
| | ×○×-□△ |
| Gas (UPPER GASTROINTESTINAL ENDOSCOPE) | □×○-△○ |
| | △○×-△□ |
| Col (COLONOSCOPE) | ○×○-□○ |
| | □××-△× |
| Pro | △○○-□○ |
| | □×□-△× |
| Acc | △△○-□○ |
| | □□×-△× |
| Unknown | — |

FIG. 8

REPAIR DIFFICULTY LEVEL
CORRESPONDENCE TABLE

41

| REPAIR DIFFICULTY LEVEL | REPAIR DESCRIPTIONS |
|---|---|
| Major | R002 (REPLACE CLEANING NOZZLE) |
| | R003 (REPLACE ANGLE KNOB) |
| Alternative | R001 (ADJUST CLEANING NOZZLE) |
| | . . . |
| Minor | . . . |
| | . . . |
| Maintain | . . . |
| | . . . |
| Other | . . . |
| | . . . |
| Unknown | . . . |

PLEASE INPUT REPAIR INFORMATION

| CLIENT | HOSPITAL A — 18a | MODEL ID | UD-3214 — 18f |
| REPAIR TECHNICIAN | TARO FUJI — 18b | SERIAL No. | 12A3456 — 18g |
| REPAIR TECHNICIAN ID | E001236 — 18c | RE-REPAIR | ▨ — 18h |
| RECEIPT DATE | 20130902 — 18d | COMPLETION DATE | 20130917 — 18e |

ENTER EQUIPMENT INFORMATION — 18i

FAILURE — 18k
| F-Code | DESCRIPTION |
| F001 | MALFUNCTION |
| F003 | WATER LEAKAGE |

CAUSE — 18m
| C-Code | DESCRIPTION |
| C001 | IMPACT |
| C002 | DAMAGE BY WATER |

REPAIR — 18n
| R-Code | DESCRIPTION |
| R001 | ADJUST NOZZLE |
| R002 | REPLACE NOZZLE |

— 18j
| P-Code | DESCRIPTION |
| P001 | CLEANING NOZZLE |

18p

SEND REPAIR INFORMATION — 18q

PLEASE INPUT INFORMATION OF REPAIR TECHNICIAN
WHOSE SKILLS ARE TO BE EVALUATED

REPAIR TECHNICIAN ─35a

REPAIR TECHNICIAN ID ─35b

PERIOD ─35c

SEND REPAIR TECHNICIAN INFORMATION ─35d

FIG. 17

SKILL EVALUATION TABLE

REPAIR TECHNICIAN : TARO FUJI
ID : 01A1205

| REPAIR DIFFICULTY LEVEL/ TYPE OF ENDOSCOPE | Ultr | Zoom | Bro | Duo | Gas | Col | Pro | Acc | Unknown | Sum |
|---|---|---|---|---|---|---|---|---|---|---|
| Major | 0 | 0 | 0 | 1 | 1 | 0 | 1 | 0 | 1 | 4 |
| Alternative | 0 | 0 | 0 | 5 | 5 | 2 | 0 | 0 | 10 | 22 |
| Minor | 0 | 0 | 2 | 0 | 1 | 2 | 0 | 0 | 3 | 8 |
| Maintain | 0 | 1 | 0 | 0 | 0 | 0 | 0 | 0 | 0 | 0 |
| Other | 0 | 0 | 0 | 0 | 0 | 0 | 0 | 0 | 0 | 1 |
| Unknown | 3 | 0 | 5 | 0 | 2 | 0 | 1 | 0 | 4 | 14 |
| Sum | 3 | 1 | 7 | 6 | 9 | 4 | 1 | 0 | 18 | 49 |

GROUP A: 0, GROUP B: 8, GROUP C: 41

RE-REPAIR HISTORY TABLE

| | Ultr | Zoom | Bro | Duo | Gas | Col | Pro | Acc | Unknown | Sum |
|---|---|---|---|---|---|---|---|---|---|---|
| NUMBER OF RE-REPAIRS | 1 | 0 | 2 | 0 | 0 | 0 | 0 | 0 | 3 | 6 |

FIG. 18

REPAIR TECHNICIAN: TARO FUJI
ID: 01A1205

SKILL EVALUATION TABLE

| REPAIR DIFFICULTY LEVEL/ TYPE OF ENDOSCOPE | Ultr | Zoom | Bro | Duo | Gas | Col | Pro | Acc | Unknown | Sum |
|---|---|---|---|---|---|---|---|---|---|---|
| Major | 0 | 0 | 0 | 1 | 1 | 0 | 1 | 0 | 1 | 4 |
| Alternative | 0 | 0 | 2 | 5 | 5 | 2 | 0 | 0 | 10 | 22 |
| Minor | 0 | 0 | 2 | 0 | 1 | 2 | 0 | 0 | 3 | 8 |
| Maintain | 0 | 0 | 0 | 0 | 0 | 0 | 0 | 0 | 0 | 0 |
| Other | 0 | 1 | 0 | 0 | 0 | 0 | 0 | 0 | 0 | 1 |
| Unknown | 3 | 0 | 5 | 0 | 2 | 0 | 1 | 0 | 4 | 14 |
| Sum | 3 | 1 | 7 | 6 | 9 | 4 | 1 | 0 | 18 | 49 |

GROUP A: 0, GROUP B: 8, GROUP C: 41

RE-REPAIR HISTORY TABLE

| | Major | Alternative | Minor | Maintain | Other | Unknown | Sum |
|---|---|---|---|---|---|---|---|
| NUMBER OF RE-REPAIRS | 4 | 3 | 2 | 0 | 0 | 3 | 10 |

FIG. 19

REPAIR GROUP: FIRST ENDOSCOPE REPAIR GROUP
ID:01A1205

SKILL EVALUATION TABLE

| REPAIR DIFFICULTY LEVEL/ TYPE OF ENDOSCOPE | Ultr | Zoom | Bro | Duo | Gas | Col | Pro | Acc | Unknown | Sum |
|---|---|---|---|---|---|---|---|---|---|---|
| Major | 0 | 0 | 0 | 1 | 1 | 0 | 1 | 0 | 1 | 4 |
| Alternative | 0 | 0 | 0 | 5 | 5 | 2 | 0 | 0 | 10 | 22 |
| Minor | 0 | 0 | 2 | 0 | 1 | 2 | 0 | 0 | 3 | 8 |
| Maintain | 0 | 1 | 0 | 0 | 0 | 0 | 0 | 0 | 0 | 0 |
| Other | 0 | 0 | 0 | 0 | 0 | 0 | 0 | 0 | 0 | 1 |
| Unknown | 3 | 1 | 5 | 6 | 2 | 0 | 0 | 0 | 4 | 14 |
| Sum | 3 | 1 | 7 | 6 | 9 | 4 | 1 | 0 | 18 | 49 |

GROUP A: 0, GROUP B: 8, GROUP C: 41

RE-REPAIR HISTORY TABLE

| | Ultr | Zoom | Bro | Duo | Gas | Col | Pro | Acc | Unknown | Sum |
|---|---|---|---|---|---|---|---|---|---|---|
| NUMBER OF RE-REPAIRS | 1 | 0 | 2 | 0 | 0 | 0 | 0 | 0 | 3 | 6 |

APPARATUS FOR MANAGING REPAIR INFORMATION OF MEDICAL EQUIPMENT, METHOD FOR OPERATING THE SAME, AND REPAIR INFORMATION MANAGEMENT SYSTEM

CROSS-REFERENCE TO RELATED APPLICATIONS

The present application claims priority under 35 U.S.C. § 119 to Japanese Patent Application No. 2013-225416, filed Oct. 30, 2013. The above application is hereby expressly incorporated by reference, in its entirety, into the present application.

BACKGROUND OF THE INVENTION

1. Field of the Invention

The present invention relates to a repair information management apparatus for managing repair information of medical equipment, a method for operating a repair information management apparatus, and a repair information management system.

2. Description Related to the Prior Art

Medical equipment such as endoscopes are used for medical examinations and treatments of patients. In case where a medical equipment is out of order, the faulty medical equipment is sent to a repair center of a medical equipment manufacturer and repaired by a repair technician. After receiving the faulty medical equipment from a user, the repair technician obtains failure descriptions and creates a repair plan based on the failure descriptions. After the user accepts the repair plan, the repair technician repairs the endoscope based on the repair plan. The failure descriptions and repair information related to the repair, such as the repair plan, are stored as a history of repairs performed by the repair technician.

To facilitate managing the repair information, Japanese Patent Laid-Open Publication No. 2002-015082 discloses a repair information management apparatus for managing repair information of medical equipment. The disclosed repair information management apparatus is a computer system which receives repair requests from users of the medical equipment, creates repair plans based on the failure descriptions, and manages the failure information. The repair information management apparatus comprises an intermediary center terminal, which receives the repair request from the user, and a repair center terminal, which is disposed in a repair center where repair is performed. The repair center terminal manages failure information transmitted from the intermediary center. The intermediary center terminal is used for obtaining the failure descriptions based on the information from the user and creating the repair plans. The created repair plans are transmitted to the user. The user selects one of the repair plans, and the selected repair plan is transmitted to the repair center terminal. The repair center terminal manages the repair information.

Since the medical equipment has been sold to the users all over the country, it is preferred to provide a plurality of repair centers in the country in view of users' convenience, for example, speedy repairs. Furthermore, due to the recent globalization, a significant amount of the medical equipment produced by a domestic manufacturer has been exported and used. Many repair centers have been opened in the equipment-importing countries to cope with requests to repair the imported medical equipment. Since the repair information is useful for improving the medical equipment and developing new products, it is preferred to collectively manage the repair information even if the repair centers are established in many countries. With the use of the repair information management apparatus disclosed in the Japanese Patent Laid-Open Publication No. 2002-015082, the terminals located in one or many countries are connected to a domestic server through a network, and thereby the collective management of the repair information is performed.

To repair the medical equipment appropriately, the repair technician is required to have repair skill of a certain level or more. For this reason, the medical equipment manufacturer evaluates the repair skills of the repair technicians and provides training courses to the repair technicians based on the results of the evaluations. Thus, the repair skill of each repair technician is improved and ensured. Since the training courses are not effective unless they match the repair skill levels of the repair technicians, correct evaluation of the repair skill of each repair technician is a prerequisite for improving the repair skills of the repair technicians. It is easy for a supervisor to correctly evaluate the repair skill of each repair technician in a case where there are few repair centers (or few repair staffs). The correct evaluation of the repair skills becomes more difficult as the number of the repair centers increases. In particular, in a case where the repair centers operate in many countries, the correct evaluation of the repair skills is extremely difficult due to cultural gaps such as languages. The repair information management apparatus disclosed in the Japanese Patent Laid-Open Publication No. 2002-015082 may enable the collective management of the information related to the repair skills of the repair technicians in the repair centers, through collecting the repair information together with the information related to the repair skills. The evaluation may be less accurate than that performed by direct evaluation by a supervisor. However, it is possible to make the evaluation close to a correct one through determining objective evaluation items and collecting information related to the evaluation items from every repair technician.

Even if the information related to the repair skills is managed collectively, the repair skills cannot be evaluated correctly unless evaluation items are not appropriate. Conventional evaluation items for the repair skills are, for example, simple track records such as years of experience as a repair technician or the number of repairs performed and a history of the repair training courses taken. However, these evaluation items have not been adequate for evaluating the repair skills correctly. This is because the medical equipment has various models, and difficulty levels of the repairs vary depending on the models and the repair descriptions. Thus, the repair skills of the repair technicians cannot be evaluated correctly only with the simple track records without consideration of the models of the medical equipment and the difficulty levels of the repairs.

SUMMARY OF THE INVENTION

An object of the present invention is to provide a repair information management apparatus, a method for operating a repair information management apparatus, and a repair information management system, capable of correctly evaluating repair skill of a repair technician of medical equipment.

In order to achieve the above and other objects, the repair information management apparatus, which manages repair information of medical equipment, according to the present invention comprises a repair information receiver, a repair information storage, and a skill evaluation screen generator.

The repair information receiver receives the repair information for each repair of the medical equipment. The repair information includes at least a model of the medical equipment, a description of the repair, and identification information of a repair technician who repaired the medical equipment. The repair information storage stores the repair information for each repair. The skill evaluation screen generator generates a skill evaluation screen for each repair technician based on the repair information. The skill evaluation screen includes a skill evaluation table showing a record of the repairs for each model of the medical equipment and a record of the repairs for each difficulty level of the description of the repair.

It is preferred that the repair information includes a result of a pre-shipment inspection performed after the repair of the medical equipment. The skill evaluation screen generator displays a re-repair history table on the skill evaluation screen. The re-repair history table shows the number of re-repairs for each model or for each difficulty level. The re-repair is performed due to rejection in the pre-shipment inspection.

It is preferred that the skill evaluation table comprises a vertical axis, a horizontal axis, and a plurality of cells. One of the models and the difficulty levels is assigned to a vertical axis. The other of the models and the difficulty levels is assigned to the horizontal axis. The cells are arranged in matrix with respect to the models and the difficulty levels. The numbers of repairs performed by the repair technician are inputted to the cells according to the models and the difficulty levels.

It is preferred that the models and the difficulty levels are arranged in the skill evaluation table in increasing or decreasing order of the difficulty levels of the description of the repair.

It is preferred that the cells in the skill evaluation table are classified into groups based on the difficulty levels, and the number of the repairs is organized on a group-by-group basis.

It is preferred that a level of repair skill of the repair technician is represented by the number of the repairs on the group-by-group basis.

It is preferred that the repair information management apparatus further comprises a database in which a repair difficulty level correspondence table is stored. The description of the repair of the medical equipment is associated with the difficulty level of the description of the repair in the repair difficulty level correspondence table. The skill evaluation screen generator determines the difficulty level of the description of the repair, stored in the repair information, based on the repair difficulty level correspondence table.

It is preferred that the skill evaluation screen generator generates the skill evaluation screen for each department to which the repair technicians belong.

The method for operating a repair information management apparatus, according to the present invention, for managing repair information of medical equipment comprises a repair information receiving step, a repair information storing step, and a skill evaluation screen generating step. In the repair information receiving step, the repair information is received for each repair of the medical equipment. The repair information includes at least a model of the medical equipment, a description of the repair, and identification information of a repair technician who repaired the medical equipment. In the repair information storing step, the repair information is stored for each repair. In the skill evaluation screen generating step, a skill evaluation screen that includes a skill evaluation table is generated for each repair technician based on the repair information. The skill evaluation table shows a record of the repairs for each model of the medical equipment and a record of the repairs for each difficulty level of the description of the repair.

The repair information management system according to the present invention comprises the above-described repair information management apparatus and a user terminal. The user terminal transmits the repair information to the repair information management apparatus and receives the skill evaluation screen from the repair information management apparatus.

According to the present invention, the record of repairs for each model of the medical equipment and the record of repairs for each repair difficulty level are clearly shown for each repair technician. Thus, the present invention provides the repair information management apparatus, the method for operating the repair information management apparatus, and the repair information management system, capable of correctly evaluating the repair skill of a repair technician of the medical equipment.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein:

FIG. 2 is an explanatory view illustrating composition of repair information;

FIG. 4 is an explanatory view illustrating a code correspondence table;

FIG. 5 is an explanatory view illustrating a term correspondence table;

FIG. 6 is an explanatory view illustrating a user correspondence table;

FIG. 7 is an explanatory view illustrating a model ID correspondence table;

FIG. 8 is an explanatory view illustrating a repair difficulty level correspondence table;

FIG. 13 is an explanatory view illustrating a repair information input screen;

FIG. 14 is an explanatory view illustrating the repair information input screen displaying candidates which have been narrowed down;

FIG. 16 is an explanatory view illustrating a technician input screen;

FIG. 17 is an explanatory view illustrating a skill evaluation screen;

FIG. 18 is an explanatory view illustrating another example of the skill evaluation screen; and FIG. 19 is an explanatory view illustrating still another example of the skill evaluation screen.

DESCRIPTION OF THE PREFERRED EMBODIMENTS

Figure 1:
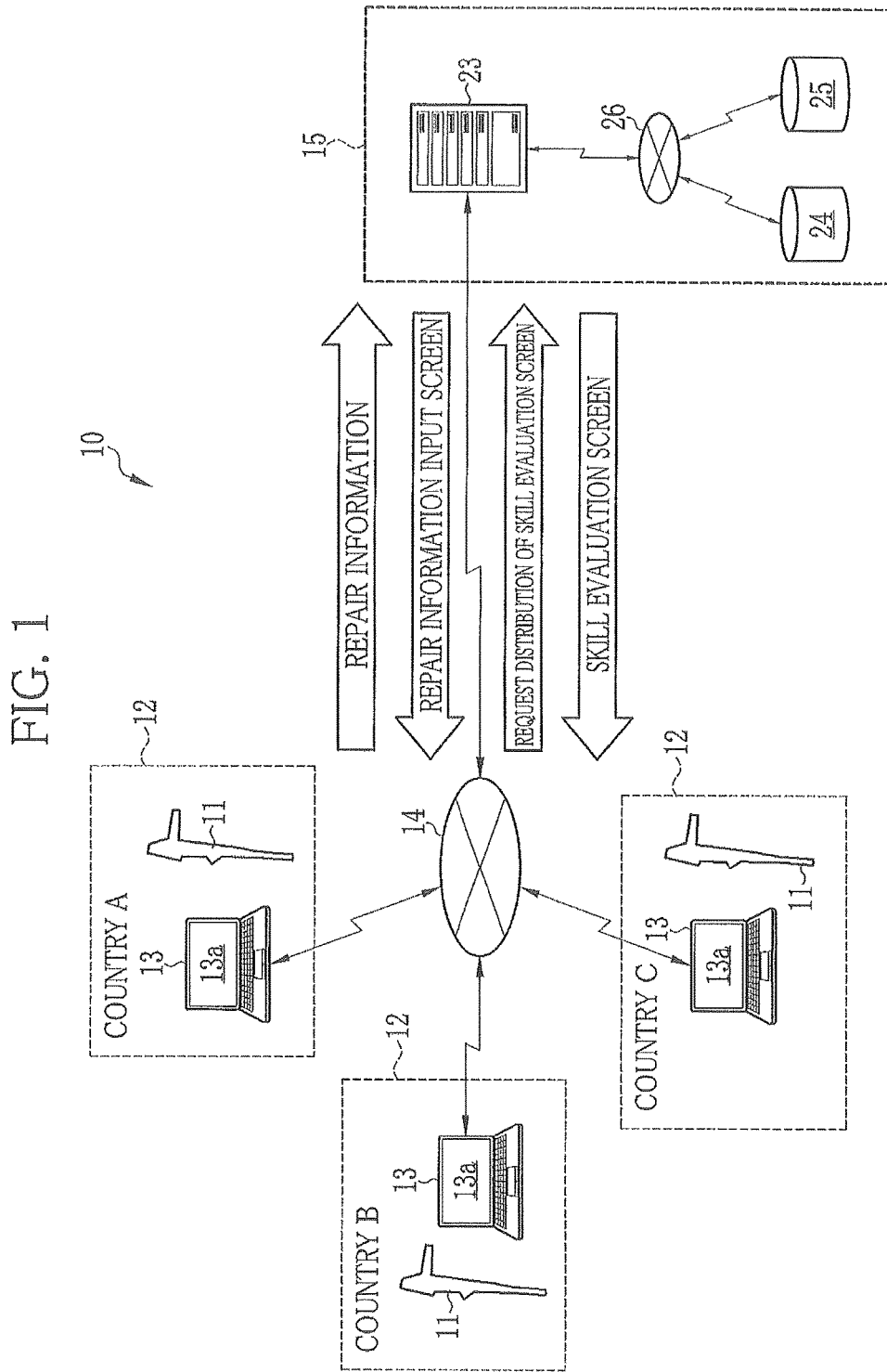
FIG. 1 is a schematic view illustrating a repair information management system.

In FIG. 1, a repair information management system 10 is a computer system which manages repair information of medical equipment, for example, endoscopes 11. The repair information management system 10 is composed of user terminals 13 disposed in repair centers 12 of the endoscopes 11 and a repair information management apparatus 15 connected to the user terminals 13 through a network 14 such as the Internet. The repair centers 12 are disposed in various countries and regions.

The repair information management system 10 distributes (or delivers) repair information input screens (operation screens) 18 (see FIG. 13) from the repair information management apparatus 15 to the user terminals 13, to collectively manage repair information related to repairs of the endoscopes 11. The repair information, which includes a faulty part, a description of a failure (failure description), a cause of the failure, and a description of a repair (repair description) is transmitted from the user terminal 13 to the repair information management apparatus 15 through the repair information input screen 18. Furthermore, the repair information management system 10 generates a skill evaluation screen 20 (see FIG. 17) and delivers the skill evaluation screen 20 to the user terminal 13. Each skill evaluation screen 20 is generated, based on the repair information collected from each user terminal 13, by the repair information management apparatus 15, and used for evaluating repair skill of a repair technician who repairs the endoscope 11.

The repair center 12 is a facility where the faulty endoscopes 11 (medical equipment) are repaired. The endoscope 11 which needs repair is sent to the repair center 12 from a client (e.g. a hospital where the endoscope 11 is used) in the region or country in which the repair center 12 is located. After the faulty endoscope 11 is delivered to the repair center 12, the repair technician analyzes the faulty part, the failure description, the cause of the failure, and the like of the endoscope 11, and repairs the endoscope 11 based on the results of the analysis. After the completion of the repair of the endoscope 11, another repair technician, different from the one who completed the repair, performs a pre-shipment inspection of the endoscope 11. The endoscope 11 which passed the pre-shipment inspection is returned to the client. The endoscope 11 rejected in the pre-shipment inspection is re-repaired and re-inspected, and then returned to the client.

The user terminal 13 is, for example, a notebook personal computer, and communicates with the repair information management apparatus 15 in accordance with a predetermined communications protocol such as HTTP (Hyper Text Transfer Protocol). Various screens (e.g. the repair information input screen 18) are delivered as web page data from the repair information management apparatus 15 to the user terminal 13. In the web page data, a source code is described with a Hyper Text Markup Language such as XML (Extensible Markup Language), which is used on the WWW (World Wide Web).

Browser software is installed on the user terminal 13, and analyzes and executes the source code. Thereby, the page data of the operation screen delivered to the user terminal 13 is displayed on a display 13a of the user terminal 13. Note that the browser software is a standard one installed on a commercially available personal computer or the like.

The repair information management apparatus 15 is disposed in a company which operates the repair information management system 10. The repair information management apparatus 15 comprises an application server 23 and DBs (databases) 24 and 25, which are connected to each other through a network 26 such as a LAN.

The application server 23 operates in two operation modes, a repair information input mode and a skill evaluation mode, in accordance with an application program (AP) 29 (see FIG. 9), which will be described below. In the repair information input mode, the repair information input screen 18 is delivered to the user terminal 13, and repair information inputted to the repair information input screen 18 is received. In the repair information input mode, the repair information input screen 18 is generated based on a term correspondence table 32 (see FIG. 5), which will be described below, and with the use of country-specific terms corresponding to the user. The user performs the repair in accordance with the repair information input screen 18 written in his/her own language.

The skill evaluation mode is an operation mode used for evaluating repair skill (for repairing the endoscopes 11) of each repair technician. In the skill evaluation mode, a technician input screen 35 (see FIG. 16) and the skill evaluation screen 20 are generated based on the term correspondence table 32 and with the use of the country-specific terms which correspond to the user. The technician input screen 35 is used for inputting a repair technician to be evaluated. The user designates a repair technician through the technician input screen 35, which is written in his/her own language, evaluates the repair skill of the repair technician based on the skill evaluation screen 20, and draws up a training schedule (e.g. a repair training course) for the repair technician, for example.

Each of DBs 24 and 25 is composed of a work station and DBMS (Database Management System) installed on the work station. The DB 24 stores the repair information inputted through the repair information input screen 18 displayed on the user terminal 13. The DB 25 stores various types of data which the application server 23 uses in executing various functions in each of the two operation modes (the repair information input mode and the skill evaluation mode).

As illustrated in FIG. 2, each piece of the repair information stored in the DB 24 includes various items of information such as the model ID and the serial number of the endoscope 11 repaired, the name of the client (or organization) who requested the repair, the name of a repair technician who repaired the endoscope 11, the repair technician ID, presence or absence of re-repair, the date (denoted as "IN" in FIG. 2) of undertaking the repair, the date (denoted as "OUT" in FIG. 2) of completion of the repair, a "P-Code" indicating a faulty part, an "F-code" indicating a failure description, a "C-code" indicating a cause of a failure, and an "R-code" indicating a repair description. "The presence or absence of re-repair" refers to whether re-repairing of the endoscope 11 is instructed in a pre-shipment inspection, which is performed after the completion of the repair of the endoscope 11. A piece of repair information is generated for each repair, assigned a repair number, and stored in the DB 24. The number of times the endoscope 11 has been repaired is the same as the number of pieces of the repair information for the endoscope 11.

The "P-Code" refers to a code corresponding to information indicating a faulty part. The plurality of P-Codes are provided in association with parts (e.g. a cleaning nozzle and an angle knob) of the endoscope 11, respectively. The cleaning nozzle is a nozzle which ejects a cleaning liquid to clean a distal portion of an insertion section of the endoscope 11. The angle knob (a knob with a dial) is used for bending the insertion section of the endoscope 11.

The "F-Code" refers to a code which corresponds to information indicating a failure description. The plurality of F-codes are provided in association with various types of possible failure descriptions (e.g. malfunction, noise in an image, and water leakage), respectively.

The "C-Code" refers to a code which corresponds to information indicating a cause of a failure. The plurality of C-codes are provided in association with a plurality of possible causes (e.g. application of impact, damage due to water, and poor contact), respectively.

The "R-Code" refers to a code which corresponds to information indicating a repair description. The plurality of R-codes are provided in association with the possible repair descriptions (e.g. adjusting the cleaning nozzle, replacing the cleaning nozzle, and replacing the angle knob), respectively.

As described above, the repair information management system 10 uses common codes for describing the repair information (the faulty part, the failure description, the cause of the failure, the repair description), which are not dependent on any specific language. As compared with the case in which the repair information is described in different languages, the load on the application server 23 is reduced and compilation and statistical processes of the repair information are easy even after the localization because the repair information is managed by the codes, which overcome the differences in languages.

Figure 3:
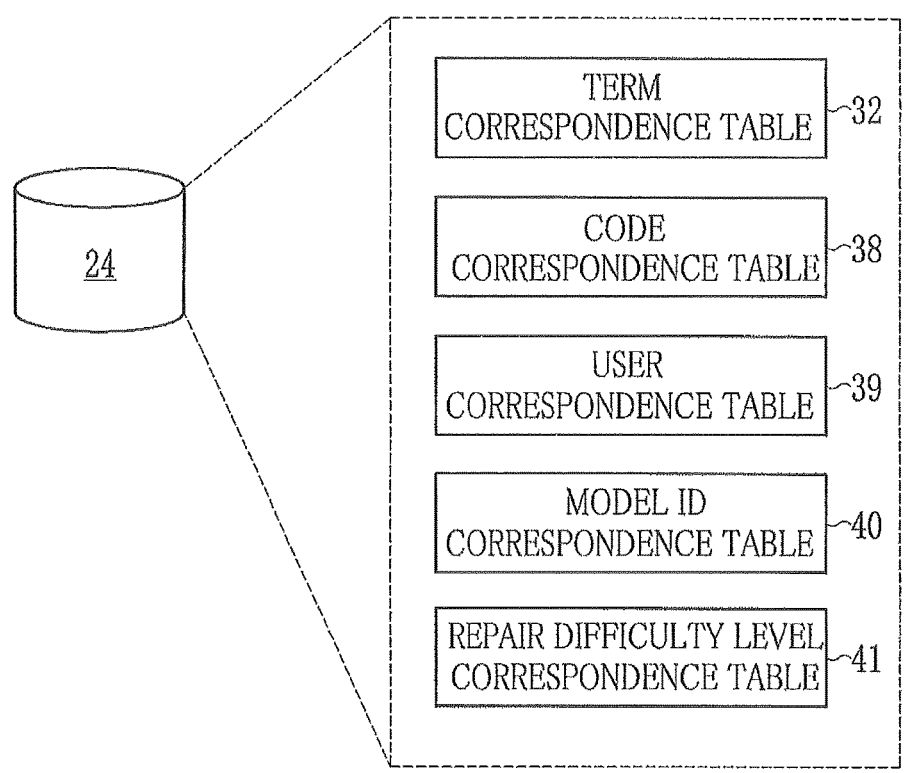
FIG. 3 is an explanatory view illustrating data stored in a DB.

As illustrated in FIG. 3, the DB 25 stores the data which the application server 23 uses in executing the various functions. The data stored in the DB 25 includes a code correspondence table 38, the term correspondence table 32, a user correspondence table 39, a model ID correspondence table 40 used for generating the skill evaluation screen 20, and a repair difficulty level correspondence table 41.

As illustrated in FIG. 4, in the code correspondence table 38, each "R-code (code for repair description or repair description code)" is associated with at least one combination of three types of codes: the "P-Code (the faulty part)", the "F-Code (the failure description)", and the "C-Code (the cause of the failure)". The code correspondence table 38 is used for a "refined search" for narrowing down possible candidates (choices) for the code of one type, by the code of another type.

In this embodiment, the repair description code "R001 (adjust the cleaning nozzle)" is associated with the combination of the three codes "P001 (cleaning nozzle)", "F001 (malfunction)", and "C001 (application of impact)", by way of example.

The repair description code "R002 (replace the cleaning nozzle)" is associated with the combination of "P001 (the cleaning nozzle)", "F001 (malfunction)" and "C002 (damage due to water)", the combination of "P001 (the cleaning nozzle)", "F003 (water leakage)", and "C001 (application of impact)", and the combination of "P001 (the cleaning nozzle)", "F003 (water leakage)", and "C002 (damage due to water)".

The repair description code "R003 (replace the angle knob)" is associated with the combination of "P002 (angle knob)", "F001 (malfunction)", and "C001 (application of damage)".

As illustrated in FIG. 5, in the term correspondence table 32, each of terms (words) to be displayed in the repair information input screen 18, the skill evaluation screen 20, and the technician input screen 35, is associated with the country-specific terms that are translations of the term (word) in different languages. The language used in the repair information input screen 18, the skill evaluation screen 20, and the technician input screen 35 is switched based on the term correspondence table 32, which will be described below. In other words, the repair information input screen 18, the skill evaluation screen 20, and the technician input screen 35 are displayed in one of the languages specified by the term correspondence table 32.

Note that each term code that is a code indicating information of a corresponding term may be associated with the country-specific terms, and stored in the term correspondence table 32, in the manner similar to the above. Managing the terms in codes makes it easy to perform compilation and statistical processes of the repair information even after the localization.

As illustrated in FIG. 6, in the user correspondence table 39, each user is assigned a user ID, the language the user uses, and a language ID of the language. The user ID is automatically assigned in accordance with predetermined rules after required items (the name of the user, the branch or department to which the user belongs, a contact address of the user, and the like) are inputted through the user terminal 13 in a user registration process, which is performed with the user's first access to the repair information management system 10. In the user registration process, the user is asked to select one of the languages to be used in using the repair information management system 10, from those listed in the term correspondence table 32. The language ID of the language selected by the user is assigned to (or stored in) the user correspondence table 39.

Note that the area in which the user terminal 13 accessing the application server 23 is located may be determined by the IP address or the like of the user terminal 13, and the language used in the identified area may be automatically assigned as the display language to the user correspondence table 39. The contents or items (e.g. the display language and the like) set (or registered) in the user registration process may be changed at or after the second access to the repair information management system 10.

As illustrated in FIG. 7, in the model ID correspondence table 40, the models of the endoscopes 11 are associated with the model IDs, respectively. The models of the endoscopes 11 include "Ultr (ultrasonic endoscope)", "Zoom (magnifying endoscope)", "Bro (bronchoscope)", "Duo (duodenoscope)", "Gas (upper gastrointestinal endoscope)", "Col (colonoscope)", "Pro", and "Acc". The model of the endoscope 11 is identified by consulting the model ID correspondence table 40. Note that the model of the endoscope 11 with the model ID not listed in the model ID correspondence table 40 is classified as "Unknown".

The ultrasonic endoscope is provided with a probe for ultrasonic endoscopy on a front-end side of a distal portion. The ultrasonic endoscope takes images of an observation object in a body cavity with an image sensor through a capture window and also performs ultrasonic imaging. The magnifying endoscope has a zooming optical system in a distal portion and performs magnification imaging in which the observation object is magnified. An insertion section of the bronchoscope is thinner than that of a general upper gastrointestinal endoscope, to be inserted into the bronchial tube. The duodenoscope is used for "endoscopic retrograde cholangiopancreatography (biliary and pancreatic duct imaging)" that is X-ray imaging with a contrast agent applied to the duodenum, the biliary, and pancreatic ducts. The upper gastrointestinal endoscope is an endoscope generally used for inspection and treatment of upper gastrointestinal tract from esophagus and stomach to duodenum. The colonoscope is an endoscope used for imaging large intestine, and has a flexible portion softer than that of the upper gastrointestinal endoscope.

As illustrated in FIG. 8, in the repair difficulty level correspondence table 41, the "R-Codes (repair descriptions)" listed in the code correspondence table 38 are associated with the repair difficulty levels (difficulty levels of repair descriptions). The repair difficulty levels are as follows: "Major", "Alternative", "Minor", "Maintain", and "Others", in decreasing order of difficulty. For example, the repair description "replace the cleaning nozzle" is classified as the "Major". Note that the repair difficulty level of the repair description not listed in the repair difficulty level correspondence table 41 is classified as "Unknown".

Figure 9:
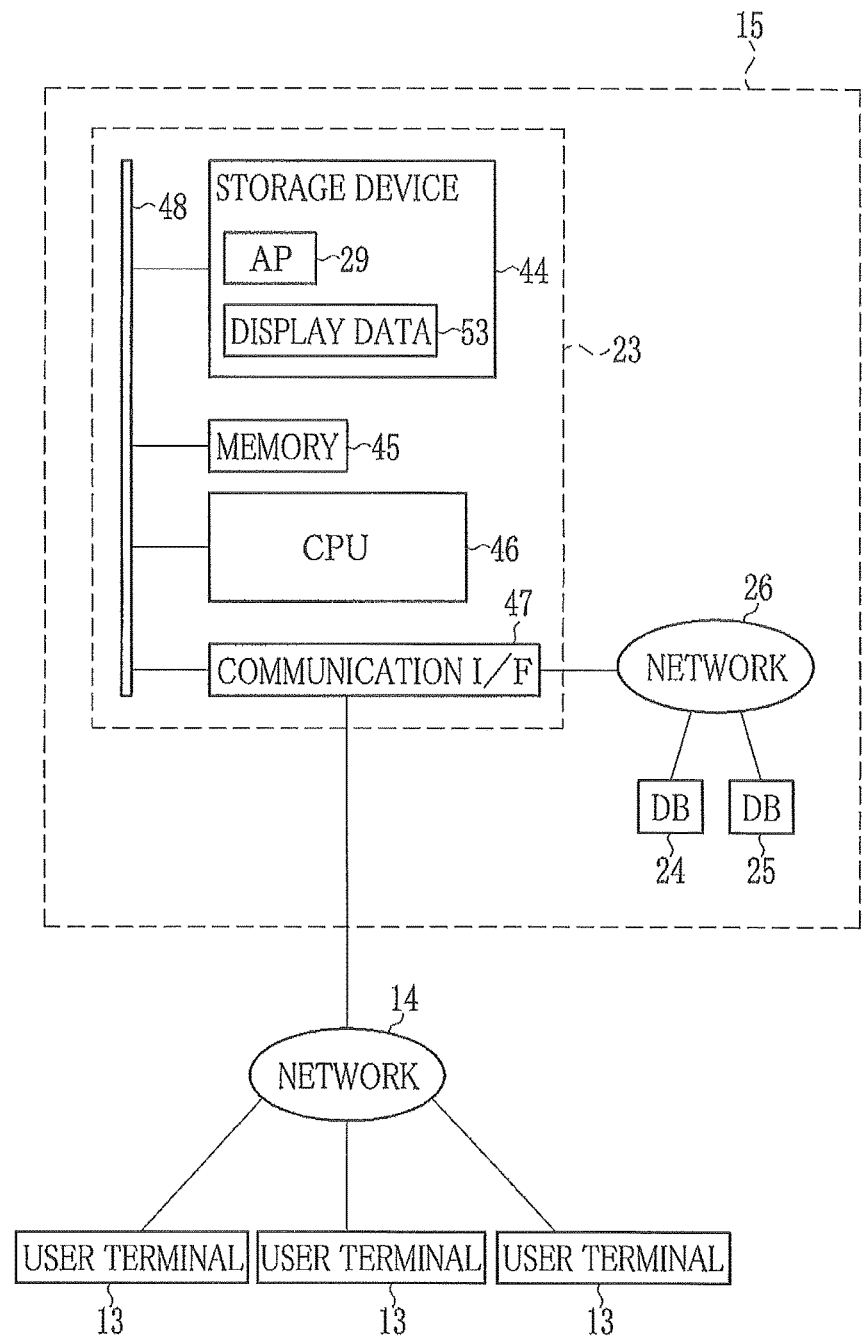
FIG. 9 is a schematic view illustrating a repair information management apparatus.

As illustrated in FIG. 9, the application server 23 is composed of the computer (e.g. a personal computer or a work station) and programs, such as a control program (e.g. an operating system) and the AP 29, installed on the computer. The AP 29 allows the computer to execute various functions and to function as the application server 23.

The application server 23 comprises a storage device 44, a memory 45, a CPU 46, and a communication I/F 47, which are connected to each other through a data bus 48. The storage device 44 is, for example, a hard disk drive, which is an internal storage incorporated in a body of the application server 23.

The storage device 44 stores the control program, the AP 29 such as application server software, images and messages displayed during the execution of the AP 29, and display data 53 used for displaying an operation mode selection screen 51 (see FIG. 12), the repair information input screen 18, the skill evaluation screen 20, and the technician input screen 35. Note that the display data 53 includes template information, being a base for generating the repair information input screen 18, the skill evaluation screen 20, the technician input screen 35, and the operation mode selection screen 51.

The memory 45 is a working memory used by the CPU 46 in executing the processes. The CPU 46 loads the control program, which is stored in the storage device 44, onto the memory 45 and executes the processes in accordance with the control program. Thereby the CPU 46 centrally controls each section of the computer. The communication I/F 47 comprises an interface for communicating with the networks 14 and 26. The application server 23 communicates with the DBs 24 and 25 and the user terminal 13 through the communication I/F 47 and the networks 14 and 26.

Figure 10:
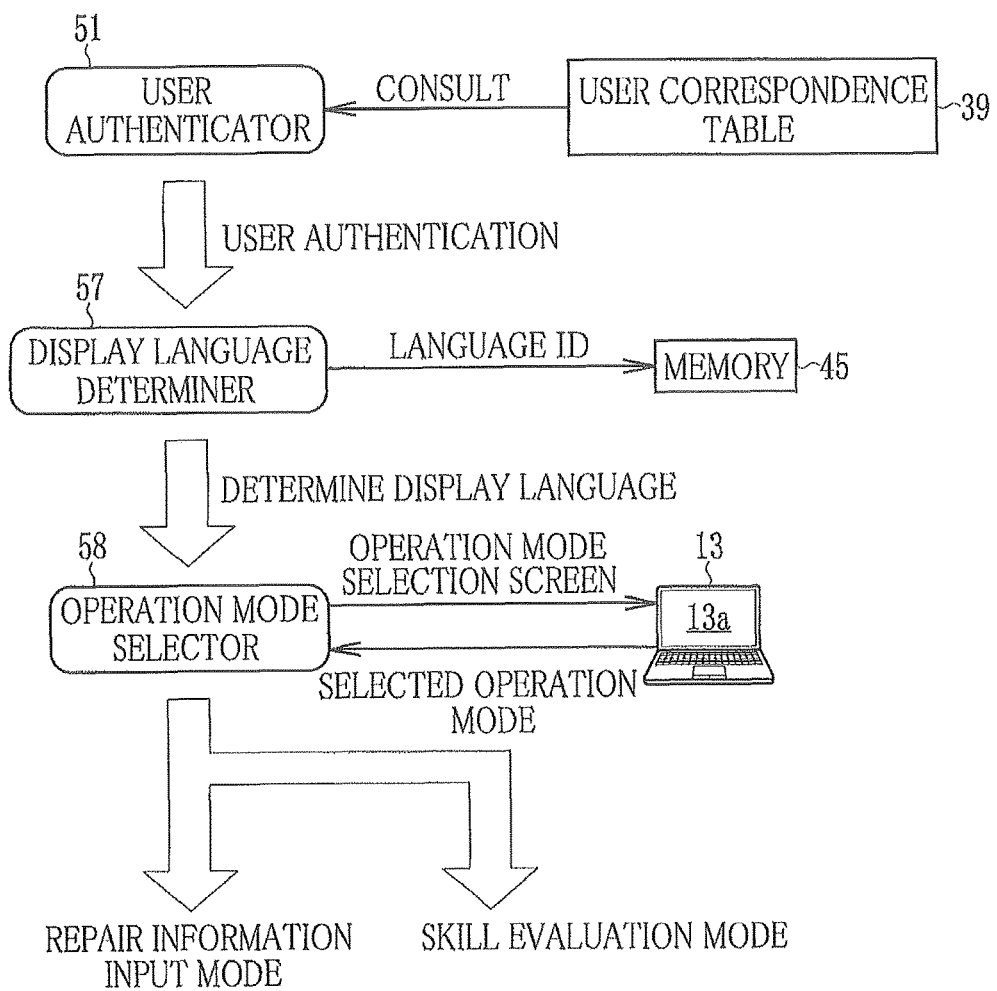
FIG. 10 is an explanatory view illustrating steps for selecting an operation mode.
Figure 11:
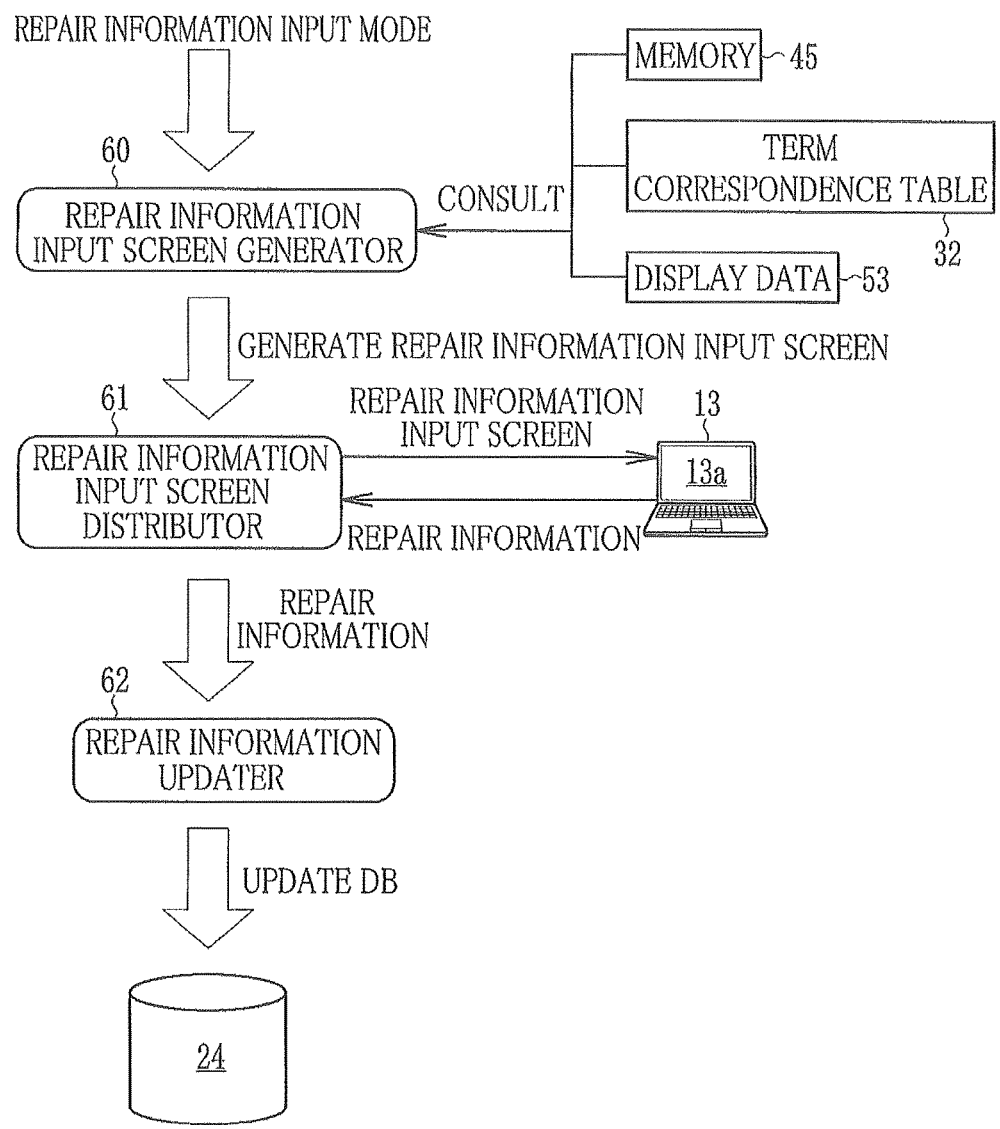
FIG. 11 is an explanatory view illustrating steps in a repair information input mode.
Figure 15:
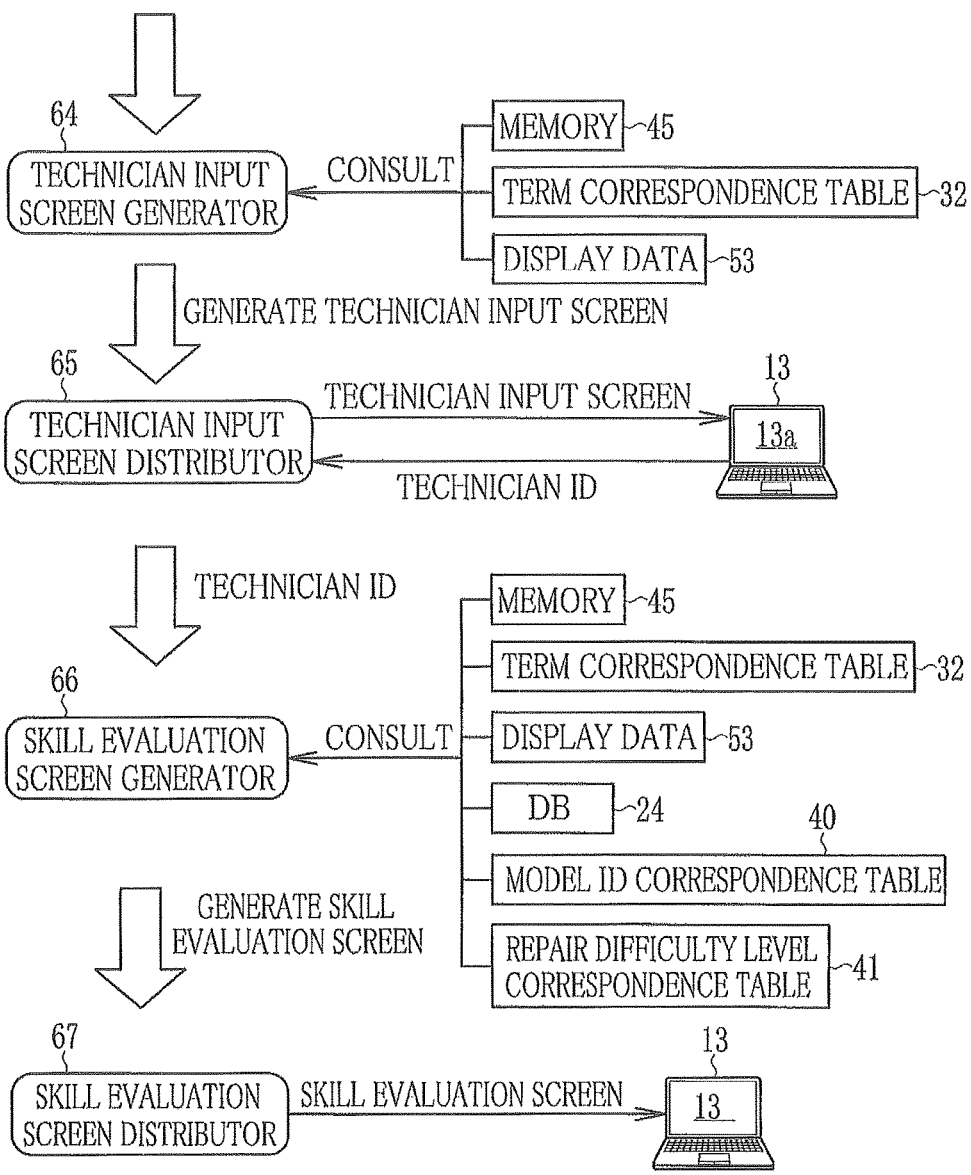
FIG. 15 is an explanatory view illustrating steps in a skill evaluation mode.

As illustrated in FIGS. 10, 11, and 15, when the AP 29 is started, the CPU 46, working together with the memory 45, functions as a user authenticator 56, a display language determiner 57, an operation mode selector 58, a repair information input screen generator 60, a repair information input screen distributor 61, a repair information updater 62, a technician input screen generator 64, a technician input screen distributor 65, a skill evaluation screen generator 66, and a skill evaluation screen distributor 67.

As illustrated in FIG. 10, the user authenticator 56 receives a request (access request), which is inputted from the user terminal 13, to access the repair information management system 10 and performs user authentication. The access request is transmitted to the user authenticator 56 when the company which operates the repair information management system 10 inputs the user ID to its website on the network 14, for example. Upon receiving the access request, the user authenticator 56 verifies the user ID, which is inputted together with the access request, against the user correspondence table 39, and thereby authenticates the user. Note that the user may be required to input the password in addition to the user ID at the time of the user authentication. In this case, the user authenticator 56 authenticates the user through the user ID and the password.

After the user authentication is completed, the display language determiner 57 is activated. The display language determiner 57 verifies the user ID of the authenticated user against the user correspondence table 39, and determines the language corresponding to the language ID which is associated with the user ID, as the language to be displayed in the subsequent screens. The display language determiner 57 allows the memory 45 to store the language ID of the language thus determined.

After the determination of the display language is completed, the operation mode selector 58 is activated. Upon the activation, the operation mode selector 58 generates the operation mode selection screen 51 illustrated in FIG. 12, and delivers the operation mode selection screen 51 to the user terminal 13. The operation mode selection screen 51 comprises an operation tag 51a, which allows the repair information management system 10 to operate in the repair information input mode, and an operation tag 51b, which allows the repair information management system 10 to operate in the skill evaluation mode. The user operates the user terminal 13 to select one of the operation tags 51a and 51b. Thus, the user selects to operate the repair information management system 10 in the repair information input mode or the skill evaluation mode.

Figure 12:
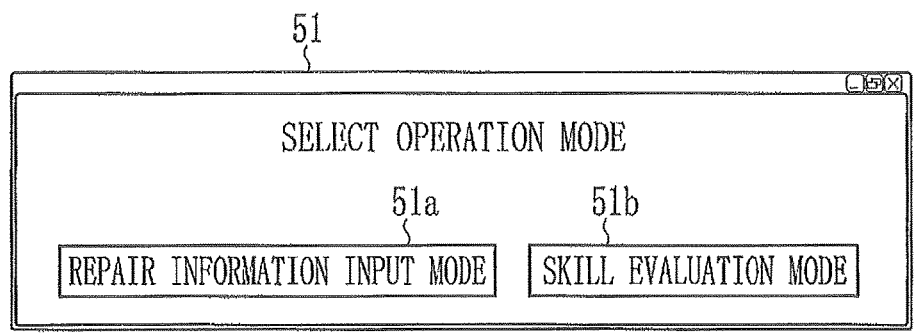
FIG. 12 is an explanatory view illustrating a repair information selection screen.

Note that the operation mode selection screen 51 illustrated in FIG. 12 is displayed in English by way of example. The operation mode selector 58 generates the operation mode selection screen 51 based on the language ID which is stored by the display language determiner 57 in the memory 45, the term correspondence table 32, and the template information stored in the storage device 44, and with the use of the country-specific terms of the language corresponding to the language ID. In a case where the language ID of a language other than English is stored in the memory 45, the operation mode selection screen 51 is displayed in the language corresponding to the ID stored in the memory 45.

As illustrated in FIG. 11, when the repair information input mode is selected through the operation mode selection screen 51, in other words, when the operation tag 51a is operated on the operation mode selection screen 51, the repair information input screen generator 60, the repair information input screen distributor 61, and the repair information updater 62 are activated.

The repair information input screen generator 60 generates the repair information input screen 18 based on the language ID which is stored in the memory 45 by the display language determiner 57, the term correspondence table 32, and the template information stored as the display data 53 in the storage device 44, and with the use of the country-specific terms of the language corresponding to the language ID. The repair information input screen distributor 61 delivers the repair information input screen 18, which is generated by the repair information input screen generator 60, to the user terminal 13.

Figure 13:
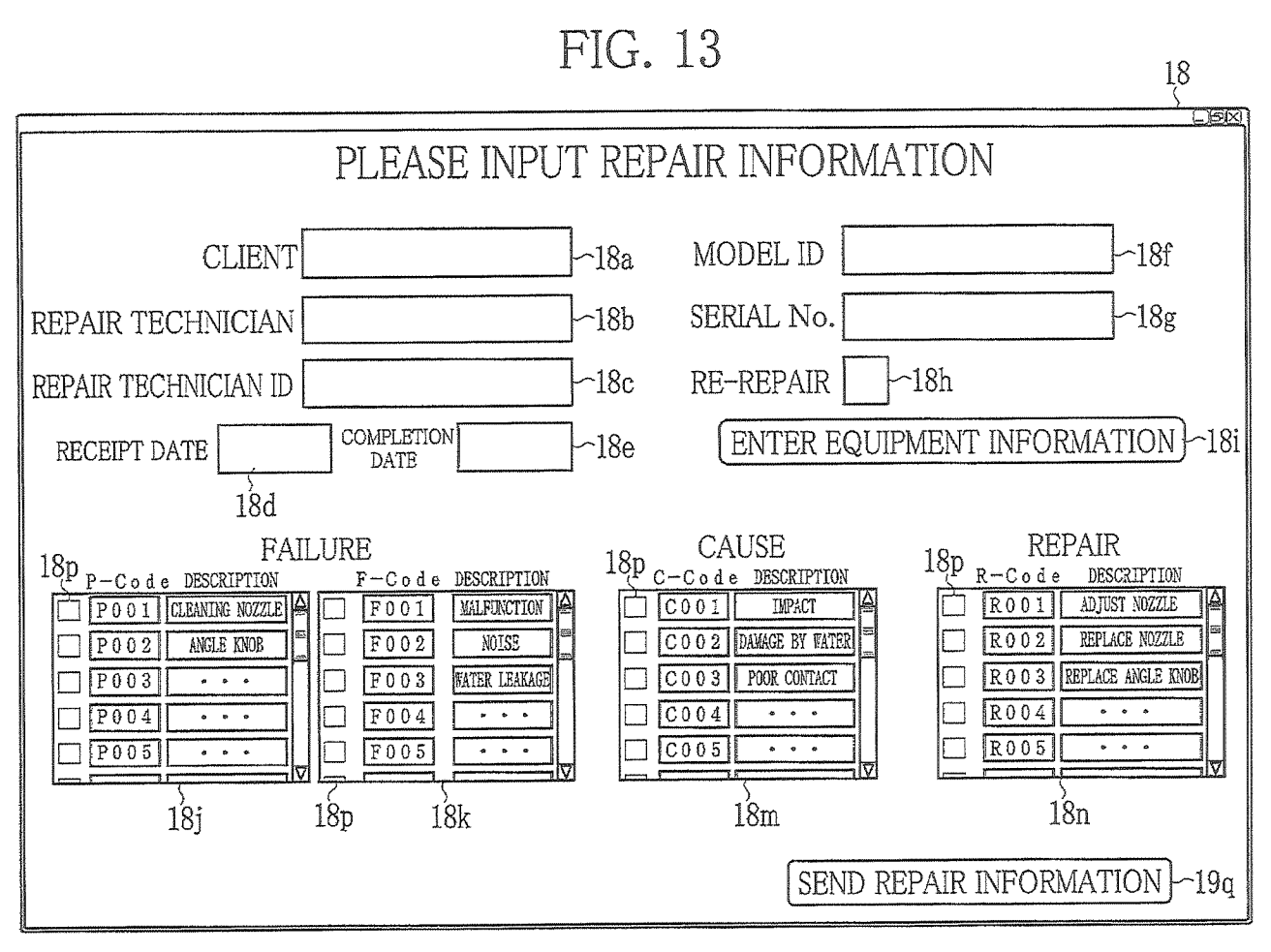

As illustrated in FIG. 13, the repair information input screen 18 is provided with a client input box 18a, a repair technician input box 18b, a repair technician ID input box 18c, a receipt date input box 18d, a completion date input box 18e, a model ID input box 18f, a serial number input box 18g, and a re-repair check box 18h. The name of the hospital or the like which requested the repair of the endoscope 11 is inputted to the client input box 18a. The name of the repair technician who repaired the endoscope 11 and his/her identification ID are inputted to the repair technician input box 18b and the repair technician ID input box 18c, respectively. The date of the receipt of the repair request of the endoscope 11 and the date of the completion of the repair are inputted to the receipt date input box 18d and the completion date input box 18e, respectively. The model ID of the repaired endoscope 11 is inputted to the model ID input box 18f. The serial number of the repaired endoscope 11 is inputted to the serial number input box 18g. The re-repair check box 18h is checked in the case where the re-repair is performed at or after the inspection after the repair of the endoscope 11.

After the model ID and the serial number are inputted to the model ID input box 18f and the serial number input box 18g, respectively, and then an enter tag 18i is operated, the endoscope 11 is identified. The codes to be displayed on the input boxes are narrowed down to those corresponding to the identified endoscope 11, which will be described below.

Furthermore, the repair information input screen 18 comprises a faulty part input box 18j, to which the faulty part is inputted, a failure description input box 18k, to which the failure description is inputted, a cause input box 18m, to which the cause of the failure is inputted, and a repair description input box 18n, to which the repair description is inputted. The faulty part input box 18j is provided to allow the user to input (or select) the actual faulty part from the list of the parts denoted by the "P-Codes (the faulty parts)". The faulty part input box 18j displays the list of the selectable "P-Codes (the faulty parts)" and their descriptions. In the faulty part input box 18j, a check box 18p is provided to the side of each code number. The faulty part is inputted by selecting one of the check boxes 18p.

The failure description input box 18k displays the list of the possible "F-Codes (the failure descriptions)" and the corresponding descriptions. The failure description is inputted by selecting one of the check boxes 18p. The cause input box 18m displays the list of the possible "C-Codes (the failure causes)" and the corresponding descriptions. The cause of the failure is inputted by selecting one of the check boxes 18p. The repair description input box 18n displays the list of the possible "R-Codes (the repair descriptions)" and the corresponding descriptions. The repair description is inputted by selecting one of the check boxes 18p.

The repair information input screen distributor 61 monitors the presence or absence of input to the input boxes 18j to 18n. When information is inputted to one of the input boxes, the repair information input screen distributor 61 uses the input information as a search key and performs the refined search to narrow down the candidates to be displayed in the rest of the input boxes. To be more specific, the repair information input screen distributor 61 consults the code correspondence table 38, and displays, in each input box, only the code numbers (possible candidates) which are associated with the search key (the input information).

For example, the faulty part "P001 (the cleaning nozzle)" is inputted to the input box 18j as illustrated in FIG. 14 in a state where no information is inputted to the rest of the input boxes 18k to 18n as illustrated in FIG. 13. In this case, the codes corresponding to the failure description, the cause of the failure, and the repair description, which are associated with the "P001 (the cleaning nozzle)", are extracted from the code correspondence table 38, and displayed in the input boxes 18k to 18n.

In this example, the failure descriptions associated with "P001 (the cleaning nozzle)" are "F001 (malfunction)" and "F003 (water leakage)", so that these codes (F001 and F003) are displayed as the candidates for the failure descriptions in the input box 18k. The causes of the failure associated with "P001 (the cleaning nozzle)" are "C001 (application of impact)" and "C002 (damage due to water)", so that these codes (C001 and C002) are displayed as the candidates for the causes of the failure in the input box 18m. The repair descriptions associated with "P001 (the cleaning nozzle)" are "R001 (adjust the cleaning nozzle)" and "R002 (replace the cleaning nozzle)", so that these codes (R001 and R002) are displayed as the candidates for the repair descriptions in the input box 18n.

The repair information input screen distributor 61 narrows down the candidates every time a new piece of information is inputted to one of the input boxes 18j to 18n, following the steps described above. For example, in a case where "F003 (water leakage)" is selected as the failure description in the input box 18k in the state illustrated in FIG. 14, "C01 (application of impact)" and "C002 (damage due to water)", each of which is associated with both "F003 (water leakage)" and "P001 (the cleaning nozzle)", are displayed as the possible candidates for the causes of the failure in the input box 18m. Furthermore, "R002 (replace the cleaning nozzle)" associated with both "F003 (water leakage)" and "P001 (the cleaning nozzle)" is displayed as the possible candidate for the repair description in the input box 18n.

As described above, the repair information is inputted to the repair information input screen 18 based on the language-independent codes, "F-Codes", "C-Codes", and "R-Codes", which are commonly used irrespective of the language used. Inputting the repair information with the use of the codes contributes to standardization of the collected repair information and prevents errors in operation and input. In other words, problems such as variation in input information from person to person (even with the same repair information) are reduced. Since the repair information is selected from the narrowed down candidates, errors in operation and input are prevented securely and the repair information is inputted efficiently.

After the information is inputted to each of the input boxes 18a to 18n on the repair information input screen 18, a repair information transmission tag 18q is activated. In response to the operation of the repair information transmission tag 18q, the repair information inputted to the input boxes 18a to 18n is transmitted to the repair information updater 62. The repair information updater 62 receives the repair information and stores the repair information in the DB 24, and thereby updates the DB 24.

Note that the repair information input screen 18 is displayed in English by way of example. In a case where the language ID which is stored in the memory 45 by the display language determiner 57 corresponds to a language other than English, for example, Japanese, the repair information input screen 18 is displayed in Japanese.

Next, an operation of the application server 23 in the skill evaluation mode is described. As illustrated in FIG. 15, in a case where the skill evaluation mode is selected through the operation mode selection screen 51, in other words, in a case where the operation tag 51b on the operation mode selection screen 51 is operated, the technician input screen generator 64 is activated. The technician input screen generator 64 generates the technician input screen 35 based on the language ID stored in the memory 45, the term correspondence table 32, and the template information of the display data 53 and with the use of the country-specific terms of the language corresponding to the language ID. The technician input screen distributor 65 delivers the technician input screen 35, which is generated by the technician input screen generator 64, to the user terminal 13.

As illustrated in FIG. 16, the technician input screen 35 is provided with a repair technician input box 35a, a repair technician ID input box 35b, a period input box 35c, and a technician information transmission tag 35d. The name and the identification ID of a repair technician to be evaluated is inputted to the repair technician input box 35a and the repair technician ID input box 35b, respectively. A time period for which the repair skill is evaluated is inputted to the period input box 35c. Thereby, the repair skill of the repair technician during the specified time period is evaluated. After the information is inputted to each of the input boxes 35a and 35b on the technician input screen 35, the technician information transmission tag 35d is activated. In response to the operation of the technician information transmission tag 35d, the information inputted to the input boxes 35a to 35c is inputted to the skill evaluation screen generator 66.

The skill evaluation screen generator 66 accesses the DB 24 and retrieves and reads out the repair information of the endoscope 11 repaired by the repair technician inputted. In a case where the repair technician has performed two or more cases of repairs of the endoscopes 11, the repair information of every case is read out. In a case where a specific time period is inputted to the technician input screen 35, all the cases within the specified time period are read out.

The skill evaluation screen generator 66 accesses the model ID correspondence table 40 in the DB 25, and identifies the model of the endoscope 11 which corresponds to the model ID in the repair information read out from the DB 24. For example, in a case where the model ID is "ooo-oo", the model is identified as "Ultr (ultrasonic endoscope)".

The skill evaluation screen generator 66 accesses the repair difficulty level correspondence table 41 in the DB 25, and identifies the repair difficulty level which corresponds to the repair description in the repair information read out from the DB 24. For example, in a case where the repair description is "replace the cleaning nozzle", the repair difficulty level is identified as "Major" that is the highest repair difficulty level.

The skill evaluation screen generator 66 generates the skill evaluation screen 20 based on the repair information read out from the DB 24, the model identified by the use of the model ID correspondence table 40, the repair difficulty level identified by the use of the repair difficulty level correspondence table 41, the language ID stored in the memory 45, the term correspondence table 32, and the template information of the display data 53, and with the use of the country-specific terms of the language which corresponds to the language ID. The skill evaluation screen distributor 67 delivers the skill evaluation screen 20, which is generated by the skill evaluation screen generator 66, to the user terminal 13.

As illustrated in FIG. 17, the skill evaluation screen 20 displays the name and an ID 70 of the repair technician, a skill evaluation table 71, and a re-repair history table 72. The skill evaluation table 71 is composed of a horizontal axis 71a, to which a plurality of models of the endoscopes 11 are assigned, a vertical axis 71b, to which the repair difficulty levels are assigned, and a plurality of cells 71c arranged in matrix with respect to the models and the repair difficulty levels.

The models are arranged in a row along the horizontal axis 71a in a manner similar to those in the model ID correspondence table 40. The models include "Ultr (the ultrasonic endoscope)", "Zoom (the magnifying endoscope)", "Bro (the bronchoscope)", "Duo (the duodenoscope)", "Gas (the upper gastrointestinal endoscope)", "Col (colonoscope)", and "Unknown (Not classified)". An item "Sum (total number)" is provided to display the total number of the endoscopes per model. Note that the models are arranged from left to right in the decreasing order of the repair difficulty level. In other words, the repair difficulty level increases toward the left end.

The repair difficulty levels are arranged in a column along the vertical axis 71b in a manner similar to those in the repair difficulty level correspondence table 41. The repair difficulty levels are "Major", "Alternative", "Minor", "Maintain", "Other", and "Unknown" arranged in this order. An item "Sum (total number)" is provided to display the total number of the endoscopes 11 per repair difficulty level. Note that the repair difficulty levels, which represent difficulty levels of the repair descriptions, are arranged from top to bottom in the decreasing order of difficulty. In other words, the repair difficulty level increases toward the top. The number of the endoscopes 11 repaired by the repair technician is inputted in each cell 71c according to the model and the repair difficulty level, in other words, on a model-by-model basis and on a difficulty-by-difficulty basis.

In the skill evaluation table 71 illustrated in FIG. 17, for example, the number of repairs of "Ultr (the ultrasonic endoscopes)" with the repair difficulty level "Unknown" is "3". The number of repairs of "Zoom (the magnifying endoscopes)" with the repair difficulty level "Other" is "1". The number of repairs of "Gas (the upper gastrointestinal endoscopes)" with the repair difficulty level "Alternative" is "5". Thus, the numbers of the endoscopes 11 repaired are displayed according to the models and the repair difficulty levels, in other words, on a model-by-model basis and on a difficulty-by-difficulty basis.

The skill evaluation table 71 specifies the number of the repairs for each model and the number of the repairs for each repair difficulty level, performed by a single repair technician. Thus, the repair skill of each repair technician is evaluated easily based on his/her track record. A glance at the skill evaluation table 71 indicates that the repair difficulty level increases toward the upper left cell 71c. Thus, the repair skill of the repair technician is evaluated intuitively.

As illustrated by dashed lines in the skill evaluation table 71, the cells 71c are classified under groups, for example, A to C according to the repair difficulty levels. The number of repairs is managed (or organized) on a group-by-group basis, and the results are provided under the skill evaluation table 71. The higher the repair skill of the repair technician, the higher the number of repairs with high repair difficulty levels and the lower the number of repairs with low repair difficulty levels. Thus, the level of the repair skill of the repair technician is represented by the number of repairs in each of the groups A to C. For example, as for the repair technician illustrated in FIG. 17, the number of repairs in the group C is significantly higher than the numbers of repairs in the groups A and B, so that the repair skill of this repair technician is determined to be low.

The re-repair history table 72 is composed of a horizontal axis 72a, to which the models of the endoscope 11 are assigned, and a plurality of cells 72b, in each of which the number of re-repairs for each model is displayed. The number of rejections in the pre-shipment inspections after the repairs of the endoscopes 11, in other words, the number of cases in which "present" is inputted to the item "re-repair" of the repair information is inputted to the cell 72b on a model-by-model basis. For example, in the re-repair history table 72 illustrated in FIG. 17, the number of the re-repairs of "Ultr (the ultrasonic endoscopes)" is "1". The number of re-repairs of "Bro (the bronchoscope)" is "2". The number of re-repairs of "Unknown (the endoscopes not classified)" is "3". Thus, the number of re-repairs is displayed on the model-by-model basis. With the use of the re-repair history table 72, the mastery level of the repair skill of each repair technician is easily evaluated on the model-by-model basis.

As described above, according to the repair information management system 10 and the repair information management apparatus 15 of this embodiment, the repair skills of the repair technicians are collected and managed globally. The track record of repairs for each repair technician is displayed according to the models of the medical equipment and the difficulty levels of the repair descriptions. In other words, the numbers of the repairs are displayed on a model-by-model basis and on a difficulty-by-difficulty basis. This allows correct evaluation of the repair technicians' repair skills. The repair skills are evaluated based on clear criteria, that is, the track records according to the models and the difficulty levels of the repair descriptions. In other words, the repair skills are evaluated based on the numbers of the repairs on a model-by-model basis and on a difficulty-by-difficulty basis. This standardizes the evaluation method of the repair skills. Furthermore, the levels of the repair skills of the repair technicians are organized hierarchically based on the results of the evaluation. This facilitates making schedules for the training courses which correspond to the levels of the repair skills of the repair technicians, and thus contributes to the improvements in the repair skills of the repair technicians.

In the above embodiment, the horizontal axis 71a of the skill evaluation table 71 indicates the models and the vertical axis 71b of the skill evaluation table 71 indicates the repair difficulty levels. Conversely, the horizontal axis 71a may indicate the repair difficulty levels and the vertical axis 71b may indicate the models. In the above embodiment, the models are arranged from left to right in the decreasing order of the repair difficulty level and the repair difficulty levels are arranged from top to bottom in the decreasing order of the repair difficulty level, by way of example. The orders of the arrangements may be reversed.

The re-repair history table 72 is displayed on the skill evaluation screen 20. The re-repair history table 72 shows the number of re-repairs for each model, which are performed due to the rejections in the pre-shipment inspections. As illustrated by a skill evaluation screen 80 in FIG. 18, a re-repair history table 81 may be displayed instead. The re-repair history table 81 shows the number of re-repairs, due to the rejections in the pre-shipment inspections, for each difficulty level of the repair description. Alternatively, a re-repair history table, showing the number of the re-repairs for each model and the number of the re-repairs for each repair difficulty level, may be displayed (not shown). Note that the composition of the skill evaluation screen 80 is the same as that of the skill evaluation screen 20 except for the re-repair history table 81, so that details of the skill evaluation screen 80 are omitted.

In the above embodiment, the skill evaluation screen 20 is generated for each repair technician. Alternatively, as illustrated by a numeral 85 in FIG. 19, a skill evaluation screen 86 may be generated for each group or department to which the repair technicians belong, for example, a repair group or the repair center 12.

The present invention is applied to the apparatus, the system, and the program for managing the repair information of the endoscopes, by way of example. The present invention may be applied to a repair information management system (or the like) for managing repair information of medical equipment other than the endoscopes.

Various changes and modifications are possible in the present invention and may be understood to be within the present invention.

What is claimed is:

1. A repair information management apparatus for managing repair information of medical equipment, comprising:
    a repair information receiver for receiving the repair information for each repair of the medical equipment, the repair information including at least a model of the medical equipment, a description of the repair, and identification information of a repair technician who repaired the medical equipment;
    a repair information storage for storing the repair information for the each repair; and
    a skill evaluation screen generator for generating a skill evaluation screen for the each repair technician based on the repair information, the skill evaluation screen including a skill evaluation table showing a record of the repairs for the each model of the medical equipment and a record of the repairs for each difficulty level of the description of the repair,
    wherein the skill evaluation table comprises a vertical axis, to which one of the models and the difficulty levels is assigned, a horizontal axis, to which the other of the models and the difficulty levels is assigned, and a plurality of cells arranged in a matrix with respect to the models and the difficulty levels, and the numbers of the repairs performed by the repair technician are inputted to the cells according to the models and the difficulty levels,
    wherein the models and the difficulty levels are arranged in the skill evaluation table in increasing or decreasing order of the difficulty levels of the description of the repair, and
    wherein the cells in the skill evaluation table are classified into groups based on the difficulty levels, and the number of the repairs is organized on a group-by-group basis.

2. The repair information management apparatus according to claim 1, wherein the repair information includes a result of a pre-shipment inspection performed after the repair of the medical equipment, and the skill evaluation screen generator displays a re-repair history table on the skill evaluation screen, and the re-repair history table shows the number of re-repairs for the each model or for the each difficulty level, and the re-repair is performed due to rejection in the pre-shipment inspection.

3. The repair information management apparatus according to claim 1, wherein a level of repair skill of the repair technician is represented by the number of the repairs on the group-by-group basis.

4. The repair information management apparatus according to claim 1, further comprising a database in which a repair difficulty level correspondence table is stored, the description of the repair of the medical equipment being associated with the difficulty level of the description of the repair in the repair difficulty level correspondence table,
    wherein the skill evaluation screen generator determines the difficulty level of the description of the repair, stored in the repair information, based on the repair difficulty level correspondence table.

5. The repair information management apparatus according to claim 1, wherein the skill evaluation screen generator generates the skill evaluation screen for each department to which the repair technicians belong.

6. A method for operating a repair information management apparatus for managing repair information of medical equipment, comprising:

receiving the repair information for each repair of the medical equipment, the repair information including at least a model of the medical equipment, a description of the repair, and identification information of a repair technician who repaired the medical equipment;

storing the repair information for the each repair; and generating a skill evaluation screen including a skill evaluation table for the each repair technician based on the repair information, the skill evaluation table showing a record of the repairs for the each model of the medical equipment and a record of the repairs for each difficulty level of the description of the repair, wherein the skill evaluation table comprises a vertical axis, to which one of the models and the difficulty levels is assigned, a horizontal axis, to which the other of the models and the difficulty levels is assigned, and a plurality of cells arranged in a matrix with respect to the models and the difficulty levels, and the numbers of the repairs performed by the repair technician are inputted to the cells according to the models and the difficulty levels, wherein the models and the difficulty levels are arranged in the skill evaluation table in increasing or decreasing order of the difficulty levels of the description of the repair, and wherein the cells in the skill evaluation table are classified into groups based on the difficulty levels, and the number of the repairs is organized on a group-by-group basis.

7. A non-transitory computer readable medium that stores therein a program causing a computer to execute a process comprising:

receiving repair information for each repair of medical equipment, the repair information including at least a model of the medical equipment, a description of the repair, and identification information of a repair technician who repaired the medical equipment;

storing the repair information for the each repair; and generating a skill evaluation screen including a skill evaluation table for the each repair technician based on the repair information, the skill evaluation table showing a record of the repairs for the each model of the medical equipment and a record of the repairs for each difficulty level of the description of the repair, wherein the skill evaluation table comprises a vertical axis, to which one of the models and the difficulty levels is assigned, a horizontal axis, to which the other of the models and the difficulty levels is assigned, and a plurality of cells arranged in a matrix with respect to the models and the difficulty levels, and the numbers of the repairs performed by the repair technician are inputted to the cells according to the models and the difficulty levels, wherein the models and the difficulty levels are arranged in the skill evaluation table in increasing or decreasing order of the difficulty levels of the description of the repair, and wherein the cells in the skill evaluation table are classified into groups based on the difficulty levels, and the number of the repairs is organized on a group-by-group basis.

8. A repair information management system comprising:

a repair information management apparatus according to claim 1; and a user terminal for transmitting the repair information to the repair information management apparatus and receiving the skill evaluation screen from the repair information management apparatus.

* * * * *